(12) United States Patent
Ohno et al.

(10) Patent No.: US 9,968,239 B2
(45) Date of Patent: May 15, 2018

(54) REMOTE CONTROLLER FOR BALLOON CONTROLLING DEVICE AND ENDOSCOPE SYSTEM

(71) Applicant: FUJIFILM Corporation, Tokyo (JP)

(72) Inventors: Hirotoshi Ohno, Ashigarakami-gun (JP); Koji Yoshida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 204 days.

(21) Appl. No.: 15/009,086

(22) Filed: Jan. 28, 2016

(65) Prior Publication Data

US 2016/0220097 A1 Aug. 4, 2016

(30) Foreign Application Priority Data

Jan. 29, 2015 (JP) ................................. 2015-015390

(51) Int. Cl.
*A61B 1/00* (2006.01)
*A61B 1/005* (2006.01)
*A61B 1/04* (2006.01)

(52) U.S. Cl.
CPC ...... *A61B 1/00082* (2013.01); *A61B 1/00006* (2013.01); *A61B 1/00048* (2013.01);
(Continued)

(58) Field of Classification Search
CPC ............ A61B 1/00082; A61B 1/00048; A61B 1/00006; A61B 1/00066; A61B 1/00052;
(Continued)

(56) References Cited

U.S. PATENT DOCUMENTS

2004/0134765 A1 7/2004 Sotome
2005/0159702 A1 7/2005 Sekiguchi et al.
(Continued)

FOREIGN PATENT DOCUMENTS

EP 0 406 845 A2 1/1991
EP 1 731 084 A1 12/2006
(Continued)

OTHER PUBLICATIONS

Extended European Search Report, dated Jun. 1, 2016, for European Application No. 16152826.0.

*Primary Examiner* — Timothy J Neal
(74) *Attorney, Agent, or Firm* — Birch, Stewart, Kolasch & Birch, LLP

(57) ABSTRACT

A remote controller includes a first balloon operation section, a second balloon operation section, a first balloon state display section, and a second balloon state display section. Each of the first and second balloon operation sections performs a pressing operation to swell or contract a balloon. Each of the first and second balloon state display sections has a swollen-state display portion and a contracted-state display portion. The swollen-state display portion is disposed along an outer circumference of each of the first and second balloon operation sections, such that the swollen-state display portion and each of the first and second balloon operation sections are coaxial with each other. The contracted-state display portion is disposed inside each of the first and second balloon operation sections, such that the contracted-state display portion and each of the first and second balloon operation sections are coaxial with each other.

13 Claims, 10 Drawing Sheets

(52) U.S. Cl.
CPC ........ *A61B 1/0052* (2013.01); *A61B 1/00052* (2013.01); *A61B 1/00066* (2013.01); *A61B 1/00131* (2013.01)

(58) Field of Classification Search
CPC .............. A61B 1/00131; A61B 1/0052; A61B 1/00068; H01H 9/161; H01H 9/18; H01H 9/182; H01H 9/185; H01H 2009/183; H01H 2009/0184; H01H 2009/186
See application file for complete search history.

(56) References Cited

U.S. PATENT DOCUMENTS

| | | |
|---|---|---|
| 2007/0049797 A1 | 3/2007 | Yoshida et al. |
| 2007/0055101 A1 | 3/2007 | Yoshida et al. |
| 2010/0059348 A1 | 3/2010 | Hauf |

FOREIGN PATENT DOCUMENTS

| | | |
|---|---|---|
| EP | 1 958 658 A1 | 8/2008 |
| JP | 3823321 B2 | 9/2006 |
| JP | 3922217 B2 | 5/2007 |
| JP | 3981364 B2 | 9/2007 |
| JP | 4409340 B2 | 2/2010 |

REMOTE CONTROLLER FOR BALLOON CONTROLLING DEVICE AND ENDOSCOPE SYSTEM

CROSS-REFERENCE TO RELATED APPLICATIONS

The present application claims priority under 35 U.S.C. § 119 to Japanese Patent Application No. 2015-015390, filed Jan. 29, 2015. The above application is hereby expressly incorporated by reference, in its entirety, into the present application.

BACKGROUND OF THE INVENTION

1. Field of the Invention

The present invention relates to a remote controller for a balloon controlling device, which remotely controls a balloon controlling device for supplying and sucking fluid to and from a balloon, and an endoscope system.

2. Description Related to the Prior Art

In a medical field, for example, an insertion section of an endoscope is inserted into a deep alimentary canal such as small intestine and large intestine, and an inner wall surface of the canal is observed and diagnosed. Since the deep alimentary canal such as small intestine and large intestine is greatly curved, and force is not easily applied to a distal end portion of the insertion section of the endoscope only by pushing the insertion section, it is difficult to insert the insertion section of the endoscope into the deep alimentary canal.

Each of United States Patent Application Publication No. 2007/0049797 (corresponding to Japanese Patent No. 3981364), Japanese Patent No. 3922217, and United States Patent Application Publication No. 2007/0055101 (corresponding to Japanese Patent No. 4409340) discloses an endoscope system in which a balloon capable of being swollen and contracted is respectively attached to the insertion section of the endoscope and the distal end portion of the overtube covered over the insertion section. According to this endoscope system, fluid such as air is supplied to or sucked from two balloons by a balloon controlling device, the balloons are alternately swollen and temporarily fixed to the deep alimentary canal, and the insertion section and the overtube are alternately inserted into the deep alimentary canal. Thus, it is possible to insert the insertion section into the deep alimentary canal that is greatly curved.

Further, according to the endoscope system disclosed in United States Patent Application Publication No. 2007/0049797, an operation switch for supplying or sucking fluid to or from balloons is disposed at a hand operation section of an endoscope. The endoscope system disclosed in each of Japanese Patent No. 3922217 and United States Patent Application Publication No. 2007/0055101 includes a remote controller provided with an operation switch for supplying or sucking fluid to or from balloons. The remote controller is used to remotely switch the balloons between a swollen state and a contracted state.

It is necessary that one of the two balloons is in a swollen state and the other of them is in a contracted state at the time of inserting the endoscope into the deep alimentary canal. Therefore, it is required for an operator to recognize the swollen state or the contracted state of the balloons. Accordingly, in the endoscope system disclosed in each of United States Patent Application Publication No. 2007/0049797 and Japanese Patent No. 3922217, the swollen state or the contracted state of the balloons is displayed on a monitor for displaying an observation image captured by the endoscope. In contrast, in the endoscope system disclosed in United States Patent Application Publication No. 2007/0055101, a state display section for displaying the swollen state or the contracted state of the balloons is provided to the remote controller for remotely operating the balloons.

However, in the endoscope disclosed in each of United States Patent Application Publication No. 2007/0049797, Japanese Patent No. 3922217, and United States Patent Application Publication No. 2007/0055101, the operation switch for swelling or contracting the balloons is disposed separately from the state display section or the monitor for displaying the swollen state or the contracted state of the balloons, and therefore the operator must move his or her gaze at the time of swelling or contracting the balloons and at the time of recognizing the swollen state or the contracted state of the balloons. In the observation or diagnosis using the endoscope, in the case where the operator moves his or her gaze frequently, the operator may overlook the displayed state, and further, the swollen or contracted state recognized by the operator may be different from the actual state of the balloons in some cases.

SUMMARY OF THE INVENTION

In view of the foregoing problems, an object of the present invention is to provide a remote controller for a balloon controlling device which requires little movement of a line of sight and enables operation for swelling or contracting balloons and recognition of a swollen state and a contracted state of the balloons, and an endoscope system.

In order to achieve the above and other objects and advantages of the present invention, a remote controller for a balloon controlling device of the present invention, which is connected to a balloon controlling device for controlling swelling or contracting of a balloon to be used for an endoscope, includes a state display section and a balloon operation section. The state display section and the balloon operation section are coaxial with each other. The state display section displays a swollen state of the balloon and a contracted state of the balloon. The balloon operation section performs an operation for swelling or contracting the balloon. Incidentally, the state display section preferably displays a swollen state of a first balloon attached to an insertion section of the endoscope or a second balloon attached to an overtube covered over the insertion section of the endoscope, and a contracted state of the first balloon or the second balloon. The balloon operation section preferably performs an operation for swelling or contracting the first balloon or the second balloon.

The state display section preferably includes a first balloon state display section for displaying the swollen state or the contracted state of the first balloon, and a second balloon state display section for displaying the swollen state or the contracted state of the second balloon. The balloon operation section preferably includes a first balloon operation section for performing an operation for swelling or contracting the first balloon, and a second balloon operation section for performing an operation for swelling or contracting the second balloon. Preferably, the first balloon state display section and the first balloon operation section are coaxial with each other, and the second balloon state display section and the second balloon operation section are coaxial with each other.

Preferably, each of the first balloon state display section and the second balloon state display section has a swollen-state display portion in the shape of a ring representing the swollen state, and a contracted-state display portion having a flattened shape representing the contracted state, and the contracted-state display portion is disposed inside the swollen-state display portion.

It is preferable that at least part of the first balloon operation section consists of a black member, and at least part of the second balloon operation section consists of a white member.

Preferably, the remote controller for a balloon controlling device further includes an operation button disposed at a position different from a position at which the balloon operation section is disposed. The operation button preferably has a shape different from a shape of the balloon operation section. Further, the balloon operation section preferably has a circular outer shape.

The swollen-state display portion is preferably disposed along an outer circumference of the balloon operation section. Further, the contracted-state display portion is preferably disposed inside the balloon operation section.

Preferably, a light emitter is disposed inside each of the swollen-state display portion and the contracted-state display portion, and the swollen-state display portion emits light in the swollen state, and the contracted-state display portion emits light in the contracted state.

The balloon operation section is preferably a push button for switching the balloon between the swollen state and the contracted state upon being pressed.

An endoscope system of the present invention includes an endoscope, an overtube, a balloon controlling device, and a remote controller for a balloon controlling device. The endoscope has a first balloon attached to an insertion section of the endoscope. The overtube is covered over the insertion section of the endoscope, and has a second balloon. The balloon controlling device controls swelling or contracting of the first balloon and the second balloon. The remote controller for a balloon controlling device includes a state display section and a balloon operation section, and the state display section and the balloon operation section are coaxial with each other.

According to the present invention, since the movement of a line of sight at the time of operating the remote controller for a balloon controlling device is little, and the operation for swelling or contracting the balloons and recognition of the swollen state or the contracted state of the balloons can be performed, an operator can get centered on the operation.

BRIEF DESCRIPTION OF THE DRAWINGS

The above objects and advantages of the present invention will become more apparent from the following detailed description when read in connection with the accompanying drawings, in which.

DESCRIPTION OF THE PREFERRED EMBODIMENTS

Figure 1:
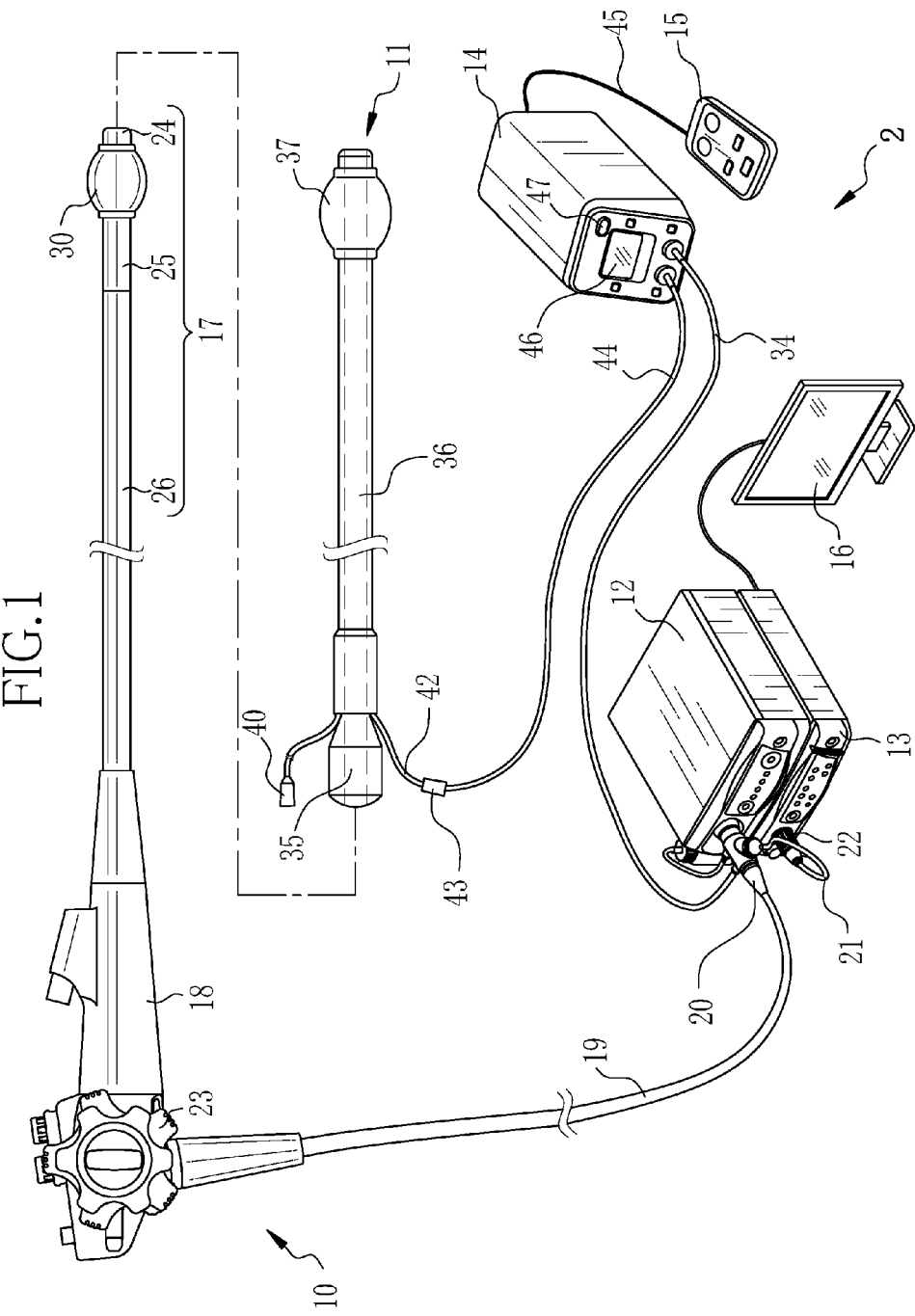
FIG. 1 is an external view of an endoscope system.

In FIG. 1, an endoscope system 2 is a double-balloon type endoscope system including an electronic endoscope 10 provided with a balloon, an overtube 11 provided with a balloon, a light source device 12, a processor device 13, a balloon controlling device 14, a remote controller 15 (i.e., remote controller for a balloon controlling device), and a monitor 16. The electronic endoscope 10 includes an insertion section 17 (i.e., insertion section for an endoscope) to be inserted into a lumen of a subject (e.g., large intestine), and an operation section 18 provided to be continuous with a proximal end of the insertion section 17 and used by an operator such as a doctor and a technologist to carry out an operation.

A universal cord 19 is connected to the operation section 18, and a light-source connector 20 is provided at a tip end of the universal cord 19. A cable 21 branches off from the light-source connector 20, and a processor connector 22 is provided at a tip end of the cable 21. The light-source connector 20 is connected to the light source device 12, and the processor connector 22 is connected to the processor device 13, respectively, in a detachable manner. Additionally, the operation section 18 is provided with an angle knob 23 and the like.

The insertion section 17 consists of a distal end portion 24, a bending portion 25, and a flexible portion 26. The distal end portion 24 is provided at a distal end of the insertion section 17, and incorporates imaging elements and the like for capturing an image inside the subject. The bending portion 25 is provided to be continuous with a proximal end of the distal end portion 24 and bendable. The flexible portion 26 is provided to be continuous with a proximal end of the bending portion 25 and has flexibility. The overtube 11 can be covered over the insertion section 17 in a detachable manner.

A first balloon 30 is detachably attached to the distal end portion 24 of the insertion section 17. The first balloon 30 used for the electronic endoscope 10 is made of an elastic material such as rubber and formed into an approximately tubular shape having narrowed ends. The first balloon 30 includes a distal end portion and a proximal end portion each having a small diameter, and a swollen portion located between the distal end portion and the proximal end portion. The distal end portion 24 is inserted through the first balloon 30 such that the first balloon 30 is located at a predetermined position of the distal end portion 24, and then a rubber ring, for example, is fit into the distal end portion and the proximal end portion of the first balloon 30. Thus, the first balloon 30 is fixed to the distal end portion 24.

The overtube 11 includes a grip portion 35 to be gripped by the operator, a main body portion 36, and a second balloon 37. The grip portion 35 is made of a rigid material such as plastic, and formed into a tubular shape. The main body portion 36 is made of a flexible material such as polyurethane, and formed into an approximately tubular shape. The main body portion 36 is fit onto a front end of the grip portion 35 so as to be fixed to the grip portion 35.

The second balloon 37 used for the electronic endoscope 10 is made of an elastic material such as rubber and formed into an approximately tubular shape having narrowed ends. The second balloon 37 includes a distal end portion and a proximal end portion each having a small diameter, and a swollen portion located between the distal end portion and the proximal end portion. The second balloon 37 is covered over an outer circumferential surface of a distal end of the main body portion 36. A thread is wound around the distal end portion and the proximal end portion of the second balloon 37, for example, to which an adhesive agent is applied. Thus, the second balloon 37 is fixed to the main body portion 36.

The flexible portion 26 has a length of several meters such that the distal end portion 24 reaches a target position inside a body of the subject. The bending portion 25 is bent in a vertical direction and a horizontal direction in accordance with the operation of the angle knob 23 of the operation section 18. Thereby, the distal end portion 24 is capable of being oriented to any direction inside the body of the subject. Additionally, an illumination window (not shown in the drawing) is provided to the distal end portion 24, such that illumination light from the light source device 12 is applied to the subject.

A signal cable (not shown in the drawing) is disposed inside each of the insertion section 17, the operation section 18, and the universal cord 19. The signal cable electrically connects the imaging elements incorporated in the distal end portion 24 to the processor connector 22. The processor device 13 subjects an imaging signal from the imaging elements to various kinds of image processing so as to covert the imaging signal to a video signal. The video signal is displayed as an observation image on the monitor 16 connected the processor device 13 via cable connection.

Figure 2:
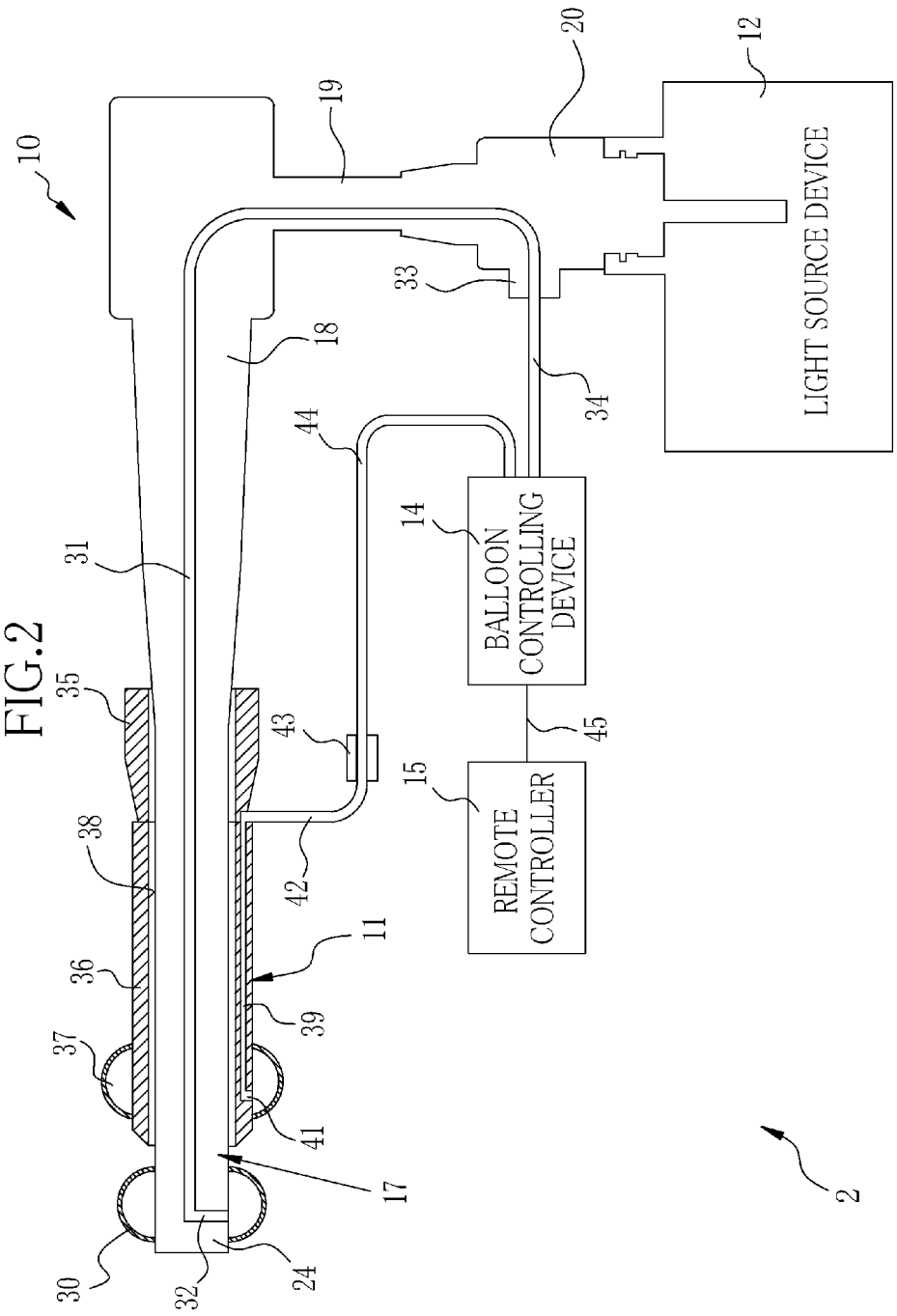
FIG. 2 is a flow-channel diagram of the endoscope system.

A specific structure for swelling and contracting the first balloon 30 of the electronic endoscope 10 and the second balloon 37 of the overtube 11 is explained hereinbelow by referring to FIG. 2. The electronic endoscope 10 includes a first fluid flow channel 31 for supplying and sucking fluid to and from the first balloon 30. The first fluid flow channel 31 is disposed inside the insertion section 17, the operation section 18, the universal cord 19, and the light-source connector 20. The first fluid flow channel 31 consists of a flexible tube, and a front end of the first fluid flow channel 31 is closed at a fixed position of the distal end portion of the first balloon 30.

The first fluid flow channel 31 is led to an opening 32 for the balloon, which is formed on an outer circumferential surface of the distal end portion 24. The opening 32 is formed at a mounting position of the first balloon 30, and the first balloon 30 is swollen or contracted by supplying or sucking the fluid through the opening 32. An endoscope-side end ring 33 is provided at a proximal end of the first fluid flow channel 31.

The endoscope-side end ring 33 is formed to be integrated with the light-source connector 20. A tube 34 is connected to the endoscope-side end ring 33, and further connected to the balloon controlling device 14. The first balloon 30 is swollen or contracted by supplying or sucking the fluid by the balloon controlling device 14.

An insertion channel 38 and a second fluid flow channel 39 are formed inside the main body portion 36 of the overtube 11 in an axial direction of the main body portion 36. The insertion channel 38 is a hole through which the insertion section 17 of the electronic endoscope 10 is inserted, and an inner diameter of the insertion channel 38 is made slightly larger than an outer diameter of the insertion section 17.

When the overtube 11 is used, lubricant such as water is supplied to an inner circumferential surface of the insertion channel 38 (corresponding to a clearance between the insertion section 17 and the main body portion 36), so as to reduce friction between the insertion section 17 and the main body portion 36. The lubricant is fed to the inner circumferential surface of the insertion channel 38 from a connector 40 shown in FIG. 1 with use of a syringe or the like (not shown in the drawing).

The second balloon 37 is attached to an outer circumferential surface of the distal end portion of the main body portion 36. The second fluid flow channel 39 is used to supply and suck fluid (e.g., air) to and from the second balloon 37, and disposed in a channel wall of the insertion channel 38. A front end of the second fluid flow channel 39 is closed at a fixed position of the distal end portion of the second balloon 37. The second fluid flow channel 39 is led to an opening 41 for the balloon, which is formed on an outer circumferential surface of the main body portion 36. The opening 41 is formed at a mounting position of the second balloon 37, and the second balloon 37 is swollen or contracted by supplying or sucking the fluid through the opening 41. A tube 42 having a small diameter is provided to be continuous with a proximal end of the second fluid flow channel 39, and a connector 43 is provided to be continuous with a proximal end of the tube 42.

A tube 44 is connected to the connector 43, and further connected to the balloon controlling device 14. The second balloon 37 is swollen and contracted by supplying and sucking the fluid by the balloon controlling device 14.

The balloon controlling device 14 is used to supply and suck the fluid (e.g., air) to and from the first balloon 30 and the second balloon 37 separately, so as to swell or contract the first balloon 30 of the electronic endoscope 10 and the second balloon 37 of the overtube 11, alternately. The balloon controlling device 14 is provided with a pump, an electromagnetic valve, and the like. The remote controller 15 is electrically connected to the balloon controlling device 14 via a cable 45.

The balloon controlling device 14 supplies the fluid to the first and second balloons 30 and 37 to swell the first and second balloons 30 and 37, and controls fluid pressure at a fixed value to maintain the first and second balloons 30 and 37 in the swollen state. Further, the balloon controlling device 14 sucks the fluid from the first and second balloons 30 and 37 to contract the first and second balloons 30 and 37, and controls fluid pressure at a fixed value to maintain the first and second balloons 30 and 37 in the contracted state.

A display section 46 is disposed on a front surface of the balloon controlling device 14. The pressure value and the swollen state or the contracted state of each of the first and second balloons 30 and 37 are displayed on the display section 46 at the time of swelling or contracting the first and second balloons 30 and 37. Additionally, an error code is displayed on the display section 46 in the case where an abnormality such as rupture of the first balloon 30 or the second balloon 37 occurs. Incidentally, the pressure value and the swollen state or the contracted state of each of the first and second balloons 30 and 37 may be superimposed on the observation image of the electronic endoscope 10 and displayed on the monitor 16. Additionally, the balloon controlling device 14 includes a power switch 47 and the like.

Further, the tubes 34 and 44 for supplying and sucking the fluid to and from the first and second balloons 30 and 37 are attached to a front panel of the balloon controlling device 14. A backflow prevention unit (not shown in the drawing) is provided to a connection portion between the balloon controlling device 14 and each of the tubes 34 and 44. The backflow prevention unit is obtained by embedding a filter for vapor-liquid separation in a hollow case having the shape of a disk which is mounted to the front panel of the balloon controlling device 14 in a detachable manner, and prevents fluid such as body fluid from flowing into the balloon controlling device 14 in the case where the first balloon 30 or the second balloon 37 raptures.

Figure 3:
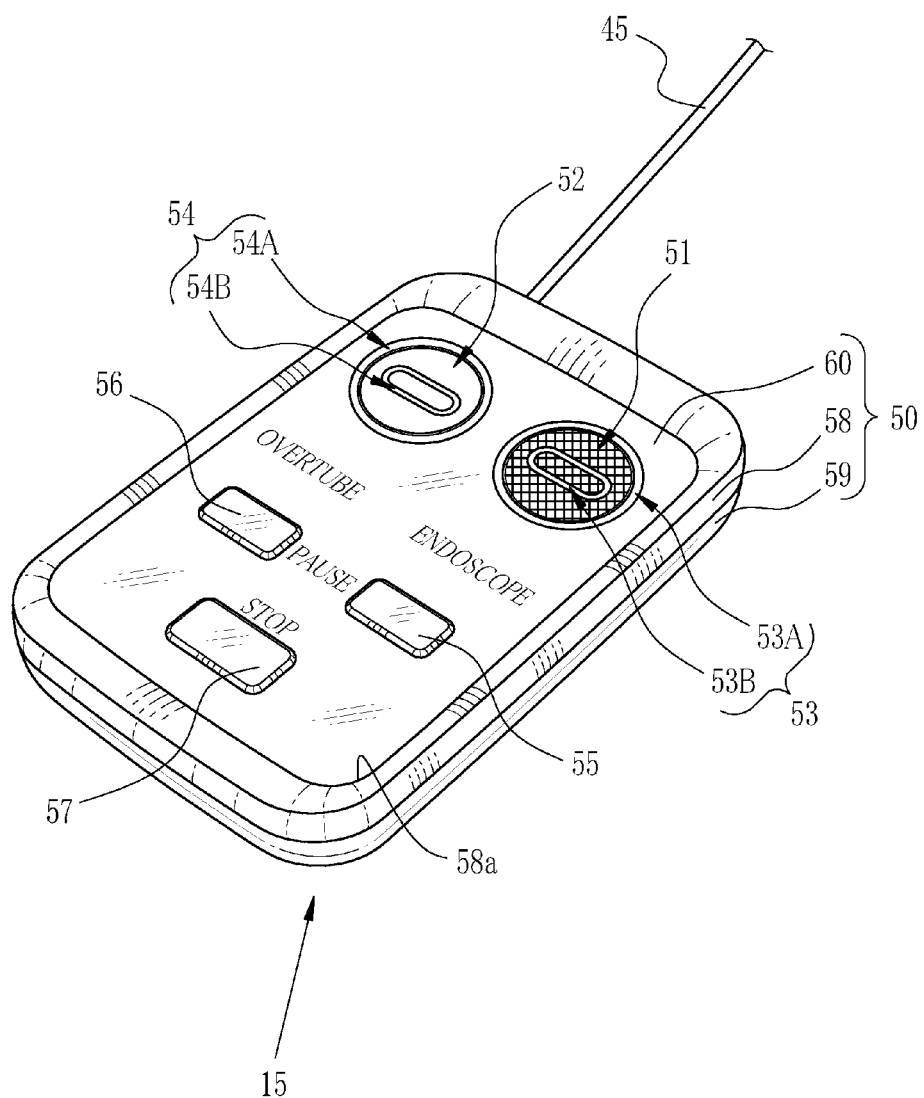
FIG. 3 is a perspective view of a remote controller for a balloon controlling device.
Figure 4:
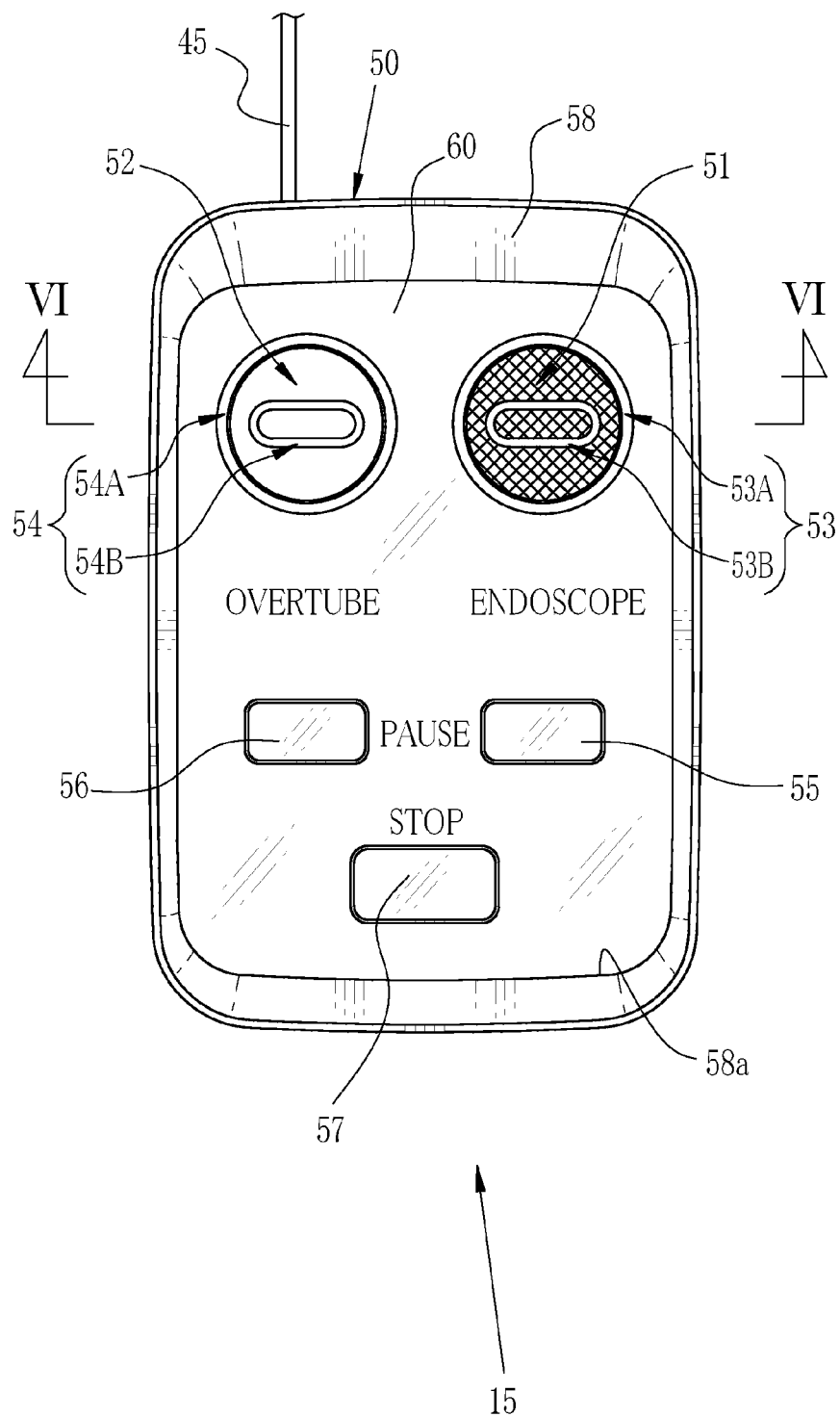
FIG. 4 is a plan view of the remote controller for a balloon controlling device.

As shown in FIGS. 3 and 4, the remote controller 15 includes a body chassis 50, a first balloon operation section 51, a second balloon operation section 52, a first balloon state display section 53, a second balloon state display section 54, a first balloon suspension button 55, a second balloon suspension button 56, and a stop button 57.

The body chassis 50 has an upper chassis member 58, a lower chassis member 59, and a transparent operation panel 60. The upper chassis member 58 and the lower chassis member 59 are coupled to each other, and the transparent operation panel 60 is fit into an upper concave portion 58a of the upper chassis member 58, such that an outer shape of the body chassis 50 is in the shape of a thin-box. The first and second balloon operation section 51 and 52, the first and second balloon state display sections 53 and 54, the first and second balloon suspension buttons 55 and 56, and the stop button 57 are exposed through the operation panel 60.

The first balloon operation section 51 is located on the right side of the body chassis 50 when the operation panel 60 is viewed from its front side. The first balloon operation section 51 is a circular push button to be used for the operation of the balloon controlling device 14 to supply or suck the fluid to or from the first balloon 30 so as to swell or contract the first balloon 30.

The first balloon state display section 53 has a swollen-state display portion 53A and a contracted-state display portion 53B. The swollen-state display portion 53A displays a swollen state in which the fluid is supplied to the first balloon 30 by the balloon controlling device 14 and thereby the first balloon 30 is swollen. The contracted-state display portion 53B displays a contracted state in which the fluid is sucked from the first balloon 30 and thereby the first balloon 30 is contracted.

The swollen-state display portion 53A is a state display section having a ring shape which represents the swollen state. The contracted-state display portion 53B is disposed inside the swollen-state display portion 53A. The contracted-state display portion 53B is a state display section having a flattened shape which represents the contracted state. The swollen-state display portion 53A is disposed along an outer circumference of the first balloon operation section 51 such that the swollen-state display portion 53A and the first balloon operation section 51 are coaxial with each other. The contracted-state display portion 53B is disposed inside the first balloon operation section 51 such that the contracted-state display portion 53B and the first balloon operation section 51 are coaxial with each other.

LED (Light Emitting Diode) chips 65A (see FIG. 6) are arranged inside the swollen-state display portion 53A. The LED chips 65A are switched between an emission state and a non-emission state by a LED driver 81. Thus, the swollen-state display portion 53A is switched between a display state and a non-display state. Further, a LED chip 65B (see FIG. 6) is arranged inside the contracted-state display portion 532. The LED chip 65B is switched between an emission state and a non-emission state by the LED driver 81. Thus, the contracted-state display portion 53B is switched between a display state and a non-display state. Incidentally, in the case where the swollen-state display portion 53A and the first balloon operation section 51 are coaxial with each other and the contracted-state display portion 53B and the first balloon operation section 51 are coaxial with each other, the first balloon operation section 51, the swollen-state display portion 53A, and the contracted-state display portion 533 are disposed such that a central axis passing through a central portion of the first balloon operation section 51, a central axis passing through a central portion of the swollen-state display portion 53A, and a central axis passing through a central portion of the contracted-state display portion 53B are coincident with one another.

The second balloon operation section 52 is located on the left side of the body chassis 50 and symmetrical to the first balloon operation section 51, when the operation panel 60 is viewed from its front side. The second balloon operation section 52 is a circular push button to be used for the operation of the balloon controlling device 14 to supply or suck the fluid to or from the second balloon 37 so as to swell or contract the second balloon 37.

The second balloon state display section 54 has a swollen-state display portion 54A and a contracted-state display portion 54B. As in the case of the first balloon state display section 53, the swollen-state display portion 54A is a state display section having a ring shape which represents the swollen state in which the second balloon 37 is swollen. The contracted-state display portion 543 is disposed inside the swollen-state display portion 54A. The contracted-state display portion 54B is a state display section having a flattened shape which represents the contracted state in which the second balloon 37 is contracted.

The swollen-state display portion 54A is disposed along an outer circumference of the second balloon operation section 52 such that the swollen-state display portion 54A and the second balloon operation section 52 are coaxial with each other. The contracted-state display portion 54B is disposed inside the second balloon operation section 52 such that the contracted-state display portion 54B and the second balloon operation section 52 are coaxial with each other. LED chips 75A (see FIG. 6) are arranged inside the swollen-state display portion 54A. The LED chips 75A are switched between an emission state and a non-emission state by the LED driver 81. Thus, the swollen-state display portion 54A is switched between a display state and a non-display state. Further, a LED chip 75B (see FIG. 6) is arranged inside the contracted-state display portion 54B. The LED chip 75B is switched between an emission state and a non-emission state by the LED driver 81. Thus, the contracted-state display portion 54B is switched between a display state and a non-display state. Incidentally, in the case where the swollen-state display portion 54A and the second balloon operation section 52 are coaxial with each other and the contracted-state display portion 54B and the second balloon operation section 52 are coaxial with each other, the second balloon operation section 52, the swollen-state display portion 54A, and the contracted-state display portion 54B are disposed such that a central axis passing through a central portion of the second balloon operation section 52, a central axis passing through a central portion of the swollen-state display portion 54A, and a central axis passing through a central portion of the contracted-state display portion 54B are coincident with one another.

One of the swollen-state display portion 53A and the contracted-state display portion 533 is in the display state, and the other of them is in the non-display state. In the similar manner, one of the swollen-state display portion 54A and the contracted-state display portion 54B is in the display state and the other of them is in the non-display state.

Further, a letter string "ENDOSCOPE" indicating the electronic endoscope 10 is put below the first balloon operation section 51, and a letter string "OVERTUBE" indicating the overtube 11 is put below the second balloon operation section 52. Instead, illustrations representing the electronic endoscope 10 and the overtube 11 may be put.

In the case where the operation panel 60 is viewed from its front side, each of the first balloon suspension button 55 located below the first balloon operation section 51, the second balloon suspension button 56 located below the second balloon operation section 52, and the stop button 57 has a shape different from those of the first and second balloon operation sections 51 and 52. Each of the first balloon suspension button 55, the second balloon suspension button 56, and the stop button 57 is a push button having a rectangular outer shape. Each of the first balloon suspension button 55, the second balloon suspension button 56, and the stop button 57 consists of a pressure-receiving portion, a pressing detection switch, and the like, which are formed to be integrated with the operation panel 60, as in the case of the first and second balloon operation sections 51 and 52, as described later.

Further, operation buttons including the first balloon operation section 51, the second balloon operation section 52, the first balloon suspension button 55, the second balloon suspension button 56, and the stop button 57, which are provided to the operation panel 60, are recessed by one step from an upper surface of the body chassis 50.

Figure 5A:
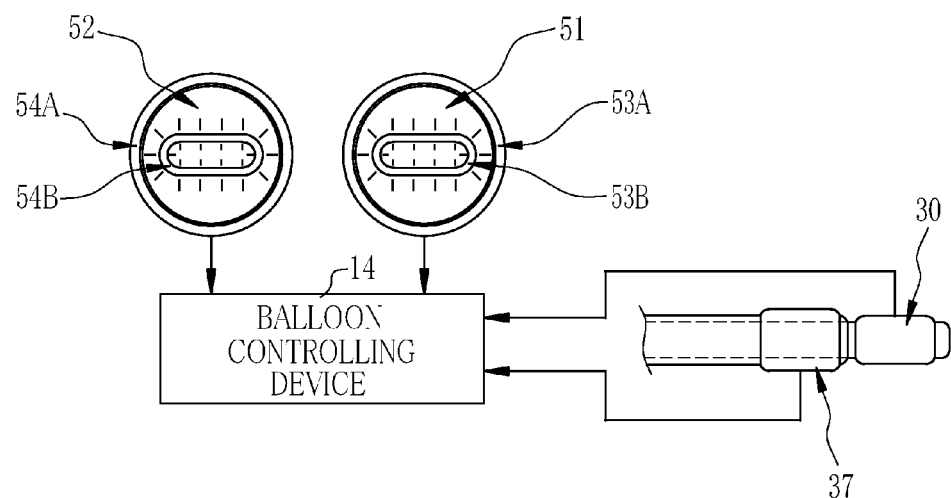
FIG. 5A is an explanatory view illustrating a displayed state of a balloon state display section in the case where a first balloon and a second balloon are in a contracted state.

After the balloon controlling device 14 and the remote controller 15 are powered on, as shown in FIG. 5A, since the LED chips 65B and 75B are set to the emission state, the contracted-state display portion 53B and the contracted-state display portion 54B are set to the display state. In contrast, since the LED chips 65A and 75A are set to the non-emission state, the swollen-state display portion 53A and the swollen-state display portion 54A are set to the non-display state. In this case, the balloon controlling device 14 sucks the fluid from the first and second balloons 30 and 37 such that the first and second balloons 30 and 37 are in the contracted state.

Upon pressing the second balloon operation section 52 so as to swell the second balloon 37 in the state shown in FIG. 5A, since the LED chips 75A are set to the emission state, the swollen-state display portion 54A is switched to the display state, as shown in FIG. 53. In contrast, since the LED chip 75B is set to the non-emission state, the contracted-state display portion 54B is switched to the non-display state. In this case, the balloon controlling device 14 supplies the fluid to the second balloon 37 such that the second balloon 37 is in the contracted state while the first balloon 30 remains in the contracted state.

Figure 5B:
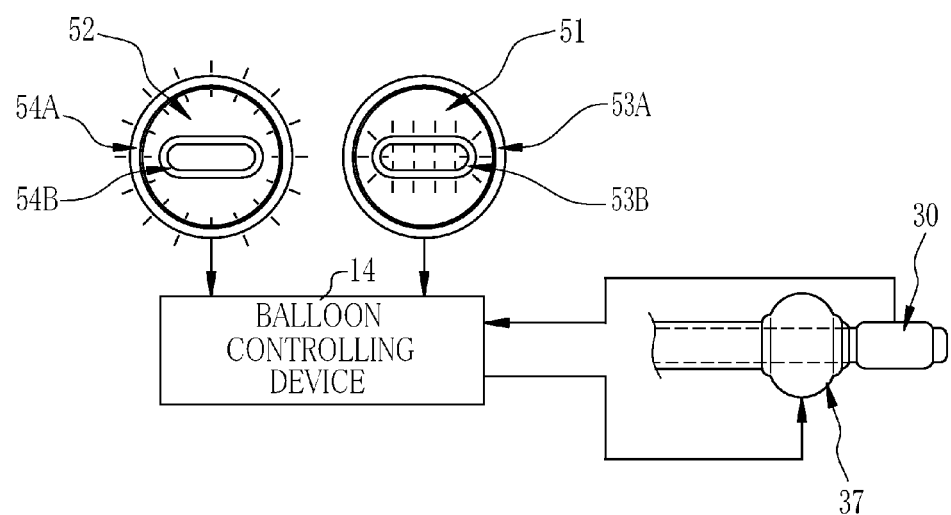
FIG. 5B is an explanatory view illustrating a displayed state of the balloon state display section in the case where the first balloon is in the contracted state and the second balloon is in a swollen state.
Figure 5C:
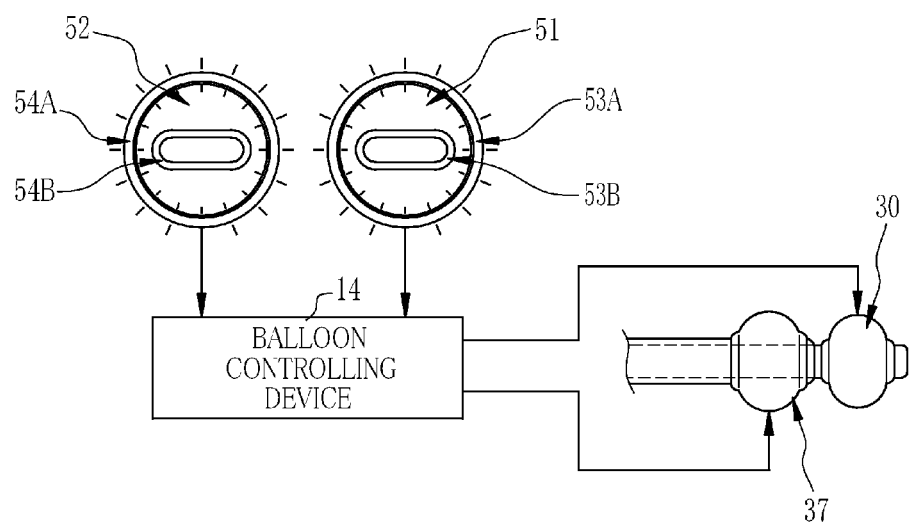
FIG. 5C is an explanatory view illustrating a displayed state of the balloon state display section in the case where the first balloon and the second balloon are in the swollen state.

Upon pressing the first balloon operation section 51 so as to swell the first balloon 30 in the state shown in FIG. 5B, since the LED chips 65A are set to the emission state, the swollen-state display portion 53A is switched to the display state, as shown in FIG. 5C. In contrast, since the LED chip 65B is set to the non-emission state, the contracted-state display portion 53B is switched to the non-display state. In this case, the balloon controlling device 14 supplies the fluid to the first and second balloons 30 and 37 such that the first and second balloons 30 and 37 are in the swollen state.

Figure 5D:
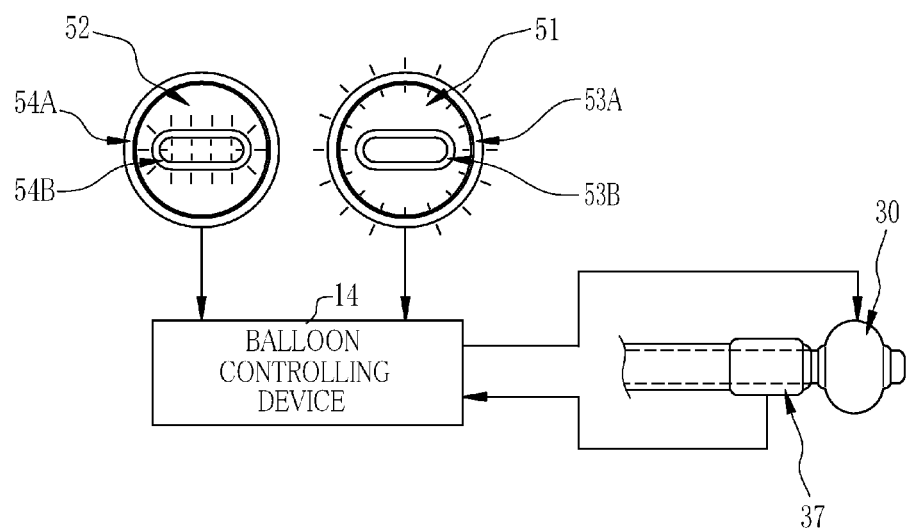
FIG. 5D is an explanatory view illustrating a displayed state of the balloon state display section in the case where the first balloon is in the swollen state and the second balloon is in the contracted state.

Upon pressing the second balloon operation section 52 so as to contract the second balloon 37 in the state shown in FIG. 5C, since the LED chip 75B is set to the emission state, the contracted-state display portion 543 is switched to the display state, as shown in FIG. 5D. In contrast, since the LED chips 75A are set to the non-emission state, the swollen-state display portion 54A is switched to the non-display state. In this case, the balloon controlling device 14 sucks the fluid from the second balloon 37 such that the second balloon 37 is in the contracted state while the first balloon 30 remains in the swollen state.

Upon pressing the first balloon operation section 51 so as to contract the first balloon 30 in the state shown in FIG. 5D, the contracted-state display portion 53B and the contracted-state display portion 54B are switched to the display state, and the swollen-state display portion 53A and the swollen-state display portion 54A are switched to the non-display state, as shown in FIG. 5A, and the balloon controlling device 14 sucks the fluid from the first and second balloons 30 and 37 such that the first and second balloons 30 and 37 are in the contracted state.

Further, the balloon controlling device 14 supplies or sucks the fluid to or from the first and second balloons 30 and 37 while changing the fluid pressure, until the first and second balloons 30 and 37 achieve the swollen state at the maximum level or the contracted state at the minimum level, at the time of setting the first and second balloons 30 and 37 to the swollen state or the contracted state. However, before the first and second balloons 30 and 37 achieve the swollen state at the maximum level or the contracted state at the minimum level, upon pressing of the first and second balloon suspension buttons 55 and 56 so as to perform a suspension operation, the balloon controlling device 14 controls the pressure of the fluid to be supplied to or sucked from the first and second balloons 30 and 37 at a fixed value, such that the first and second balloons 30 and 37 remain in the swollen state or the contracted state.

Figure 5E:
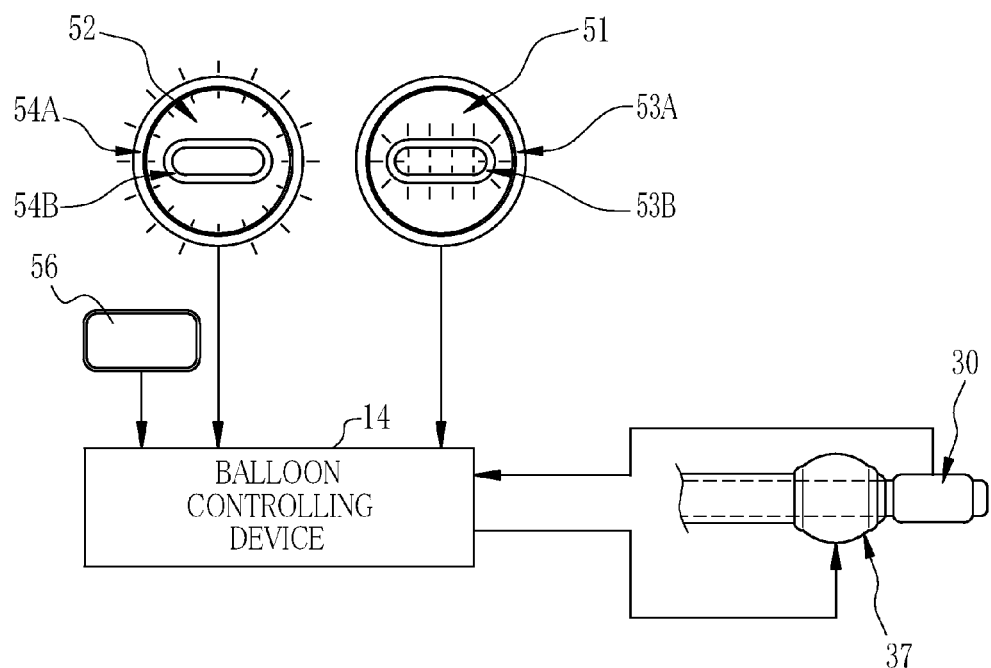
FIG. 5E is an explanatory view illustrating the case where the first balloon is in the contracted state, the second balloon is in the swollen state, and a suspension operation is performed so as to control pressure of fluid to be supplied to the second balloon at a fixed value.

For example, as shown in FIG. 5E, in the case where the second balloon operation section 52 is pressed such that the second balloon 37 is set to the swollen state, upon pressing of the second balloon suspension button 56 so as to perform the suspension operation before the second balloon 37 achieves the swollen state at the maximum level, the balloon controlling device 14 controls the pressure of the fluid to be supplied to the second balloon 37 at a fixed value such that the second balloon 37 remains in the swollen state.

As described above, the operation is performed by pressing the first balloon operation section 51 and the second balloon operation section 52 of the remote controller 15, and thereby it is possible to set one of the first and second balloons 30 and 37 to the swollen state and the other of them to the contracted state, and it is possible to swell the first and second balloons 30 and 37 alternately.

As described above, the swollen-state display portion 53A is disposed along the outer circumference of the first balloon operation section 51 such that the swollen-state display portion 53A and the first balloon operation section 51 are coaxial with each other, and the contracted-state display portion 53B is disposed inside the first balloon operation section 51 such that the contracted-state display portion 53B and the first balloon operation section 51 are coaxial with each other. Further, the swollen-state display portion 54A is disposed along the outer circumference of the second balloon operation section 52 such that the swollen-state display portion 54A and the second balloon operation section 52 are coaxial with each other, and the contracted-state display portion 54B is disposed inside the second balloon operation section 52 such that the contracted-state display portion 54B and the second balloon operation section 52 are coaxial with each other. Accordingly, it is possible to minimize the movement of a line of sight at the time of operating the remote controller 15 and prevent an erroneous operation at the time of swelling or contracting the first and second balloons 30 and 37 and false recognition of the swollen state or the contracted state of the first and second balloons 30 and 37. Thus, the operator can get centered on the operation and insert the insertion section 17 of the electronic endoscope 10 and the overtube 11 into the lumen of the subject, such as deep alimentary canal, safely and promptly.

Further, the contracted-state display portion 53B is disposed inside the swollen-state display portion 53A, and the contracted-state display portion 54B is disposed inside the swollen-state display portion 54A. Accordingly, it is possible to minimize the movement of a line of sight at the time of operating the remote controller 15 and prevent an erroneous operation at the time of swelling or contracting the first and second balloons 30 and 37 and false recognition of the swollen state or the contracted state of the first and second balloons 30 and 37. Thus, it is possible to insert the insertion section 17 of the electronic endoscope 10 and the overtube 11 into the lumen of the subject safely and promptly. Additionally, each of the swollen-state display portions 53A and 54A has a ring shape, and each of the contracted-state display portions 53B and 54B has a flattened shape, it is easy to form an impression of the swollen state and the contracted state of the first and second balloons 30 and 37 by viewing the swollen-state display portions 53A and 54A and the contracted-state display portions 53B and 54B. Further, it is possible to intuitively recognize the swollen state and the contracted state of the first and second balloons 30 and 37. Also from this point of view, it is possible to prevent an erroneous operation and false recognition.

Further, while each of the first balloon operation section 51 and the second balloon operation section 52 has a circular shape, each of the first balloon suspension button 55 and the second balloon suspension button 56 has a rectangular shape, and therefore it is possible to intuitively recognize the first balloon operation section 51 and the second balloon operation section 52, and it is easy to distinguish the first balloon operation section 51 and the second balloon operation section 52 from other operation buttons including the first balloon suspension button 55, the second balloon suspension button 56, and the stop button 57, at the time of swelling or contracting the first and second balloons 30 and 37.

Furthermore, a black member is used to make the first balloon operation section 51, and a white member is used to make the second balloon operation section 52. In general, a black member is used to make most part of the electronic endoscope 10, and a white member or a transparent member, which has a color lighter than that of the electronic endoscope 10, is used to make most part of the overtube 11. Namely, the first balloon operation section 51 has a color which can be associated with the electronic endoscope 10, and the second balloon operation section 52 has a color which can be associated with the overtube 11. Thus, it is possible to intuitively recognize the first and second balloons 30 and 37. Additionally, a letter string "ENDOSCOPE" indicating the electronic endoscope 10 is put below the first balloon operation section 51, and a letter string "OVERTUBE" indicating the overtube 11 is put below the second balloon operation section 52. It is possible to surely prevent an error at the time of swelling or contracting the first and second balloons 30 and 37 by using both of the colors and the letter strings.

Figure 6:
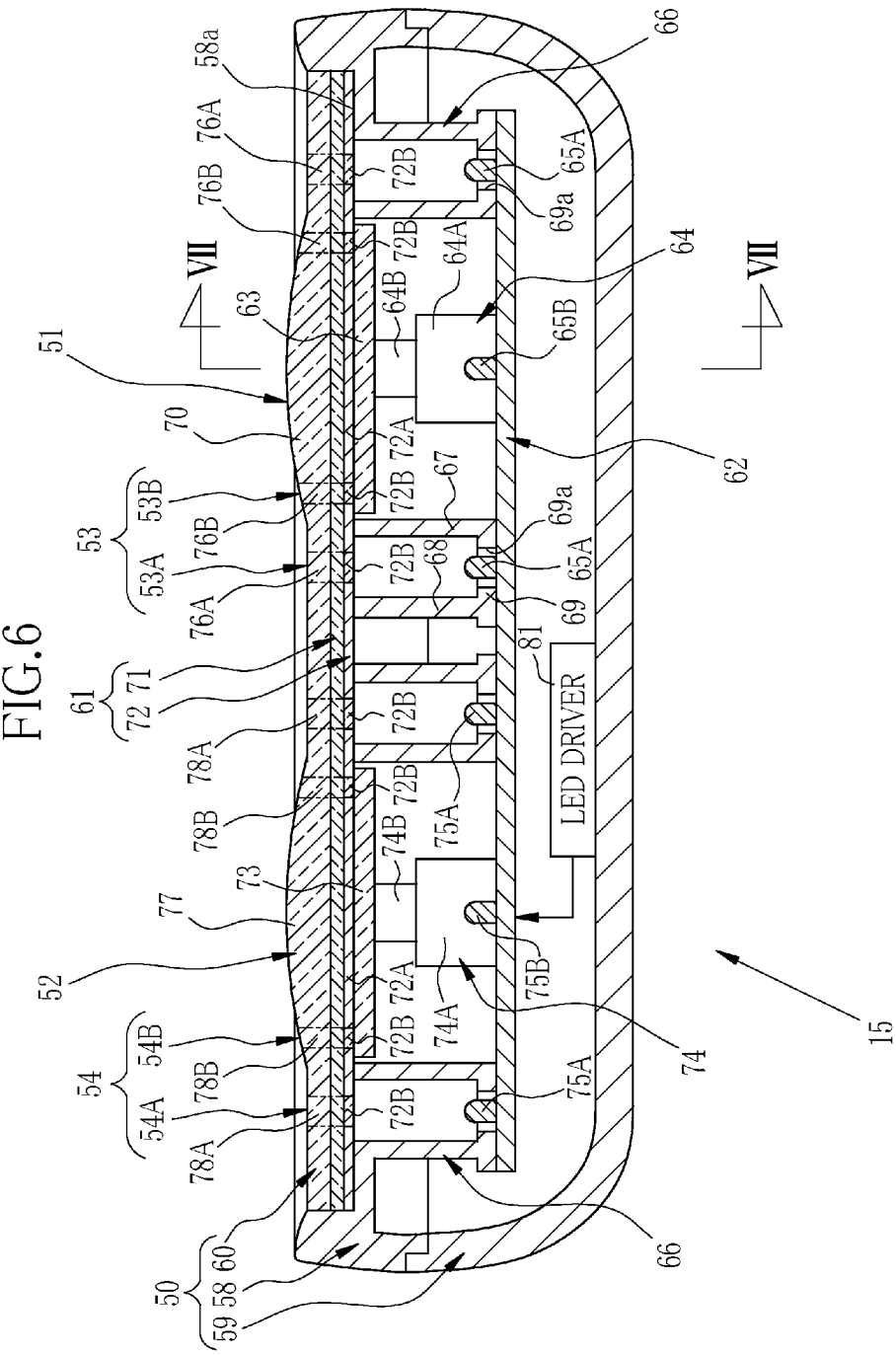
FIG. 6 is a cross-sectional view taken along a line VI-VI of FIG. 4.
Figure 7:
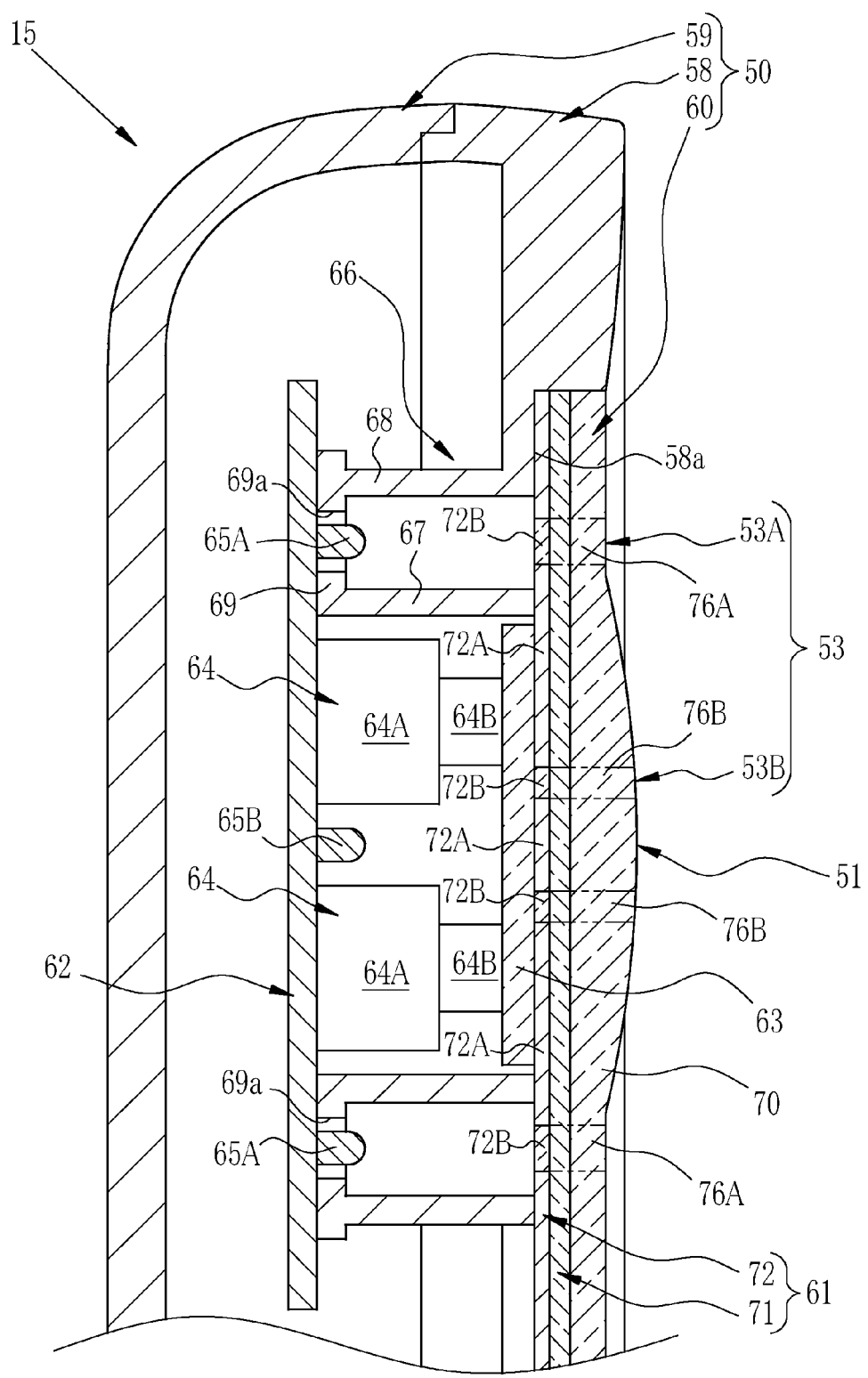
FIG. 7 is a cross-sectional view of a main part taken along a line VII-VII of FIG. 6.

Next, an internal structure of the remote controller 15 is explained by referring to FIGS. 6 and 7. The operation panel 60 and a print sheet 61 are disposed on the upper concave portion 58a of the upper chassis member 58 in the remote controller 15. Further, a transparent plate 63, a pair of pressing detection switches 64, and the LED chip 65B are disposed at a portion on the substrate 62, which corresponds to the first balloon operation section 51, inside the remote controller 15. Similarly, a transparent plate 73, a pair of pressing detection switches 74, and the LED chip 75B are disposed at a portion on the substrate 62, which corresponds to the second balloon operation section 52, inside the remote controller 15.

Furthermore, the LED chip 65A is disposed at a portion on the substrate 62, which corresponds to the swollen-state display portion 53A of the first balloon state display section 53, and the LED chip 75A is disposed at a portion on the substrate 62, which corresponds to the swollen-state display portion 54A of the second balloon state display section 54, inside the remote controller 15. The substrate 62 is mounted on a light-shielding member 66 which is formed to be integrated with a rear surface of the upper chassis member 58.

Figure 8:
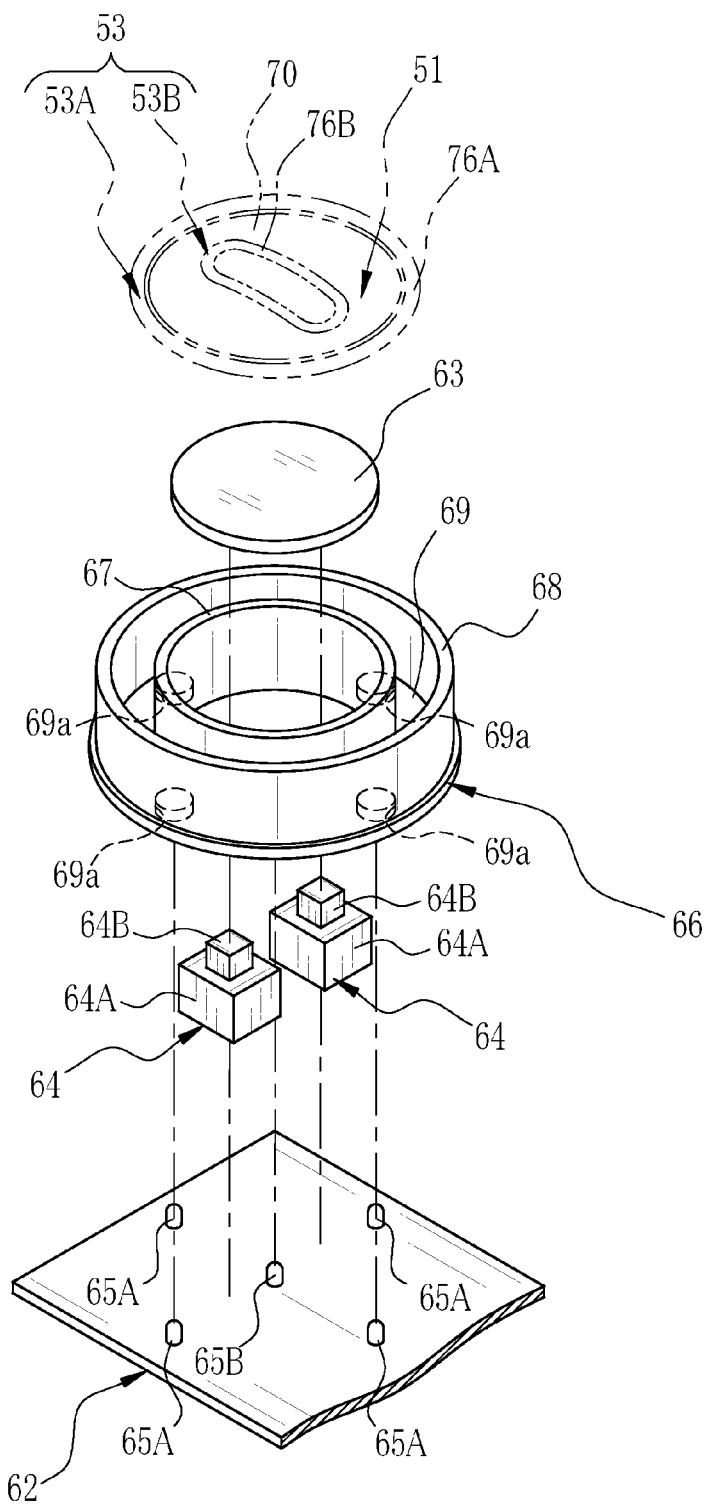
FIG. 8 is an exploded perspective view illustrating a structure of a balloon operation button and a structure of the balloon state display section.

As shown in FIG. 8, the light-shielding member 66 has tubular light-shielding walls 67 and 68 which are coaxial with each other, and a bottom surface wall 69 which blocks a bottom surface side of each of the light-shielding walls 67 and 68, such that the light-shielding walls 67 and 68 are coupled to each other. The bottom surface side of the light-shielding wall 67 located inside is open, and when the substrate 62 is fixed to the bottom surface of the light-shielding member 66, the light-shielding wall 67 is positioned between the LED chip 65A and the LED chip 65B. The LED chip 65B is positioned on a central axis of the light-shielding wall 67 having a tubular shape. The light-shielding wall 67 shields light between the LED chip 65B and the LED chip 65A.

The light-shielding wall 68 is disposed outside the LED chip 65A so as to prevent the emission light of the LED chip 65A from being leaked to the outside. Through holes 69a are formed on the bottom surface wall 69 at the same angular interval in accordance with the arrangement of the LED chips 65A. When the substrate 62 is fixed to the bottom surface of the light-shielding member 66, each of the LED chips 65A is positioned at the center of the through hole 69a. A plurality of the LED chips 65A are disposed around the LED chip 65B with a predetermined distance therebetween at the same angular interval. In this embodiment, there are four LED chips 65A disposed at an angular interval of 90°.

As shown in FIGS. 6 and 7, the pressure-receiving portion 70 is disposed at a portion of the operation panel 60 which corresponds to the first balloon operation section 51. The pressure-receiving portion 70 is made of transparent resin and integrated with the operation panel 60. The pressure-receiving portion 70 protrudes toward the front surface side of the operation panel 60 and is thicker than a surrounding area so as to have a dome-like shape. The pressure-receiving portion 70 has flexibility and movable in its thickness direction upon being pressed.

The print sheet 61 is sandwiched and held between the upper concave portion 58*a* of the upper chassis member 58 and the operation panel 60. The print sheet 61 includes a transparent resin sheet 71 made of polycarbonate, for example, and a print layer 72 provided to a rear surface of the transparent resin sheet 71. The print layer 72 has a light-shielding print portion 72A subjected to printing for giving light-shielding properties, and a translucent print portion 72B subjected to printing for giving translucency.

A region of the light-shielding print portion 72A of the print sheet 61, which is a shaded portion in FIGS. 3 and 4, namely, which corresponds to the pressure-receiving portion 70 is printed in black. In contrast, the translucent print portion 723 of the print sheet 61, the pressure-receiving portion 70, and the transparent resin sheet 71 constitute display windows 76A and 76B (also see FIG. 8).

Since the region of the print sheet 61, which corresponds to the pressure-receiving portion 70, is printed in black, the black region is exposed through the pressure-receiving portion 70 and the transparent resin sheet 71 in the first balloon operation section 51.

The display window 76A and the LED chips 65A constitute the swollen-state display portion 53A, and the display window 76B and the LED chip 65B constitute the contracted-state display portion 53B. The display window 76A is a display window in the shape of a ring, which is disposed along an outer circumference of the pressure-receiving portion 70 such that the display window 76A and the pressure-receiving portion 70 are coaxial with each other. Thus, the light emitted from the LED chips 65A passes through the display window 76A and displays a ring shape, namely, the swollen state.

The display window 76B is a display window which is disposed inside the pressure-receiving portion 70 and has a flattened shape. Specifically, the display window 76B is a display window in the shape of a track having semicircular side ends. Thus, the light emitted from the LED chip 65B passes through the display window 76B and displays a flattened shape, namely, the swollen state.

The pair of pressing detection switches 64 is fixed to the substrate 62 with the LED chip 65B sandwiched therebetween inside the light-shielding wall 67. The pressing detection switch 64 is a mechanical switch, and includes a switch body 64A, a press portion 64B, and a spring member (not shown in the drawing). The press portion 64B protrudes from the switch body 64A toward the pressure-receiving portion 70. Upon being pressed, the press portion 64B is pressed into the switch body 64A, and thereby the pressing detection switch 64 is turned on. In the case where the press portion 64B is released from being pressed, the press portion 64B protrudes from the switch body 64A due to the biasing of the spring member, and thereby the pressing detection switch 64 is turned off.

In the case where the pressure-receiving portion 70 is pressed, the press portion 64B of the pressing detection switch 64 is pressed through the print sheet 61 and the transparent plate 63. Since the pair of pressing detection switches 64 receives the pressing through the transparent plate 63, even if the pressure-receiving portion 70 and the transparent plate 63 are pressed in a direction inclined with respect to a tube-axis direction of the light-shielding wall 67, the press portion 64B of at least one of the pressing detection switches 64 is pressed, and thereby the pressing detection switch 64 outputs an ON-signal. In response to the ON-signal outputted from the pressing detection switch 64, the balloon controlling device 14 is controlled, such that the first balloon 30 is set to the swollen state or the contracted state.

The transparent plate 63 is made of transparent resin and formed into a disc shape having a predetermined thickness. An outer circumferential surface of the transparent plate 63 is held by the inner circumferential surface of the light-shielding wall 67, and the transparent plate 63 is sandwiched between the print sheet 61 and the pressing detection switch 64, such that the transparent plate 63 is attached in a movable manner along the tube-axis direction of the light-shielding wall 67.

Light emission control of the LED chips 65A, 65B, 75A, and 75B is performed by the LED driver 81. The LED driver 81 is electrically connected to the balloon controlling device 14, and performs the light emission control in conjunction with the operation control performed by the balloon controlling device 14. In the case where the balloon controlling device 14 contracts the first balloon 30, the LED driver 81 controls such that the LED chip 65A is set to the non-emission state, and the LED chip 653 is set to the emission state. Further, in the case where the balloon controlling device 14 sets the first balloon 30 to the swollen state, the LED driver 81 controls such that the LED chip 65A is set to the emission state and the LED chip 65B is set to the non-emission state. Also in the case where the second balloon 37 is set to the contracted state or the swollen state, the LED driver 81 performs the light emission control of the LED chips 75A and 75B as in the case of the first balloon 30.

A pressure-receiving portion 77 is provided to a portion of the operation panel 60 which corresponds to the second balloon operation section 52. The pressure-receiving portion 77 is made of transparent resin, integrated with the operation panel 60, and has flexibility, as with the pressure-receiving portion 70. The pressure-receiving portion 77 has a dome-like shape which protrude toward the front surface of the operation panel 60.

A region of the print sheet 61, which corresponds to the pressure-receiving portion 77, is printed in white. The white region is exposed through the pressure-receiving portion 77 and the transparent resin sheet 71 in the second balloon operation section 52. In contrast, the translucent print portion 72B of the print sheet 61, the pressure-receiving portion 77, and the transparent resin sheet 71 constitute display windows 78A and 78B. The display window 78A and the LED chip 75A constitute the swollen-state display portion 54A, and the display window 78B and the LED chip 753 constitute the contracted-state display portion 54B. The light-shielding wall 67 of the light-shielding member 66 is provided between the LED chips 75A and 75B, and the light-shielding wall 68 of the light-shielding member 66 is provided around the LED chips 75A, so as to shield light between the LED chip 75B and the LED chips 75A, as in the case of the LED chips 65A and 65B.

The display window 78A is a display window in the shape of a ring, which is disposed along an outer circumference of the pressure-receiving portion 77, such that the display window 78A and the pressure-receiving portion 77 are coaxial with each other. In contrast, the display window 78B is a display window which is disposed inside the pressure-receiving portion 77 and has a flattened shape. Specifically, the display window 78B is a display window in the shape of a track having semicircular side ends.

Since the transparent plate 73 has the same structure as that of the transparent plate 63 and the pressing detection switch 74 has the same structure as that of the pressing detection switch 64, the explanation of the transparent plate 73 and the pressing detection switch 74 will be omitted. The pressing detection switch 74 includes a switch body 74A, a press portion 743, and a spring member (not shown in the drawing). In the case where the pressure-receiving portion 77 is pressed, the press portion 74B of the pressing detection switch 74 is pressed through the print sheet 61 and the transparent plate 73, and the pressing detection switch 74 outputs an ON-signal. In response to the ON-signal outputted from the pressing detection switch 74, the balloon controlling device 14 is controlled such that the second balloon 37 is set to the swollen state or the contracted state.

As a preparation for using the electronic endoscope 10, the overtube 11 is mounted on the insertion section 17, the tube 34 of the balloon controlling device 14 is connected to the endoscope-side end ring 33, and the tube 44 of the balloon controlling device 14 is connected to the connector 43. Further, the light-source connector 20 is connected to the light source device 12, and the processor connector 22 is connected to the processor device 13.

The operator inserts the insertion section 17 of the electronic endoscope 10 and the overtube 11 alternately into the lumen of the subject by pushing them. As necessary, the operator operates the remote controller 15 to control the balloon controlling device 14 such that the second balloon 37 is set to the swollen state and the first balloon 30 is set to the contracted state. Thereby, the overtube 11 is temporarily fixed inside the lumen of the subject, and the insertion section 17 is further inserted deep inside of the lumen. Alternatively, the operator operates the remote controller 15 to control the balloon controlling device 14 such that the second balloon 37 is set to the contracted state and the first balloon 30 is set to the swollen state, such that the insertion section 17 is temporarily fixed inside the lumen of the subject, and the overtube 11 is further inserted deep inside of the lumen. In this way, the insertion section 17 is inserted deep inside of the lumen so as to enable observation deep inside the lumen.

In the above embodiment, the first balloon operation section 51 and the first balloon state display section 53 are coaxial with each other, and the second balloon operation section 52 and the second balloon state display section 54 are coaxial with each other. However, the first balloon state display section may be disposed inside, along the outer circumference of, or along inner circumference of the first balloon operation section, or alternatively the first balloon operation section may be disposed inside, along the outer circumference of, or along inner circumference of the first balloon state display section. Similarly, the second balloon state display section may be disposed inside, along the outer circumference of, or along inner circumference of the second balloon operation section, or alternatively the second balloon operation section may be disposed inside, along the outer circumference of, or along inner circumference of the second balloon state display section.

In the above embodiment, the first balloon operation section 51 includes the print sheet printed in black. However, it is sufficient that at least part of the print sheet is black. Further, here, black means a color of low brightness, and includes approximately black. Similarly, the second balloon operation section 52 includes the print sheet printed in white. However, it is sufficient that at least part of the print sheet is white. Further, here, white means a color of high brightness, and includes approximately white. Furthermore, although each of the contracted-state display portions 53B and 54B is in the shape of a track as the flattened shape, the present invention is not limited thereto. It is sufficient that each of the contracted-state display portions 53B and 54B is not in the shape of the ring and represents the swollen state of the balloon. Each of the contracted-state display portions 53B and 54B may be ellipsoidal or linear.

Moreover, the light emitted from the first balloon state display section 53 may be different from the light emitted from the second balloon state display section 54. Thereby, it becomes easier to distinguish the first balloon operation section 51 from the second balloon operation section 52 and distinguish the first balloon state display section 53 from the second balloon state display section 54. Accordingly, it is possible to surely prevent an erroneous operation at the time of swelling or contracting the first and second balloons 30 and 37 and false recognition of the swollen state or the contracted state of the first and second balloons 30 and 37. In this case, for example, the emission color of the light of the LED chip disposed inside the first balloon state display section 53 is made different from the emission color of the light of the LED chip disposed inside the second balloon state display section 54. Additionally, the light emitter for emitting light from the first balloon state display section 53 and the second balloon state display section 54 is not limited to the LED chip. An organic EL (Electro Luminescence) element may be arbitrarily used as the light emitter, for example.

Although the balloon controlling device 14 and the remote controller 15 are connected to each other via the cable 45 in a wired manner in the above embodiment, the present invention is not limited thereto. Each of the balloon controlling device 14 and the remote controller 15 may be provided with an independent wireless communication interface, so as to perform transmission/reception of signals in a wireless manner.

In the above embodiment, each of the first and second balloon operation sections 51 and 52 is a push button, and each of the first balloon state display section 53 and the second balloon state display section 54 is the transparent display window in which the LED chips are disposed. However, the present invention is not limited thereto. For example, a structure in which a display panel such as a liquid crystal display and a touch panel laminated on the display panel are disposed on an operation panel may be used. In this case, it is preferable that, the first and second balloon operation sections 51 and 52 and the first and second balloon state display sections 53 and 54 are displayed as icons on the display section, and an operation for swelling or contracting the first and second balloons 30 and 37 is performed so as to control the switching of the first and second balloon state display sections 53 and 54 between the emission state and the non-emission state by touching the first and second balloon operation sections 51 and 52.

In the above embodiment, two balloons including the first balloon 30 attached to the insertion section of the electronic endoscope and the second balloon 37 attached to the overtube are provided as the balloons to be used for the endoscope. However, the present invention is not limited thereto. It is sufficient that the present invention includes one of the first and second balloons 30 and 37. In this case, it is sufficient that the present invention includes one of the first balloon operation section 51 and the second balloon operation section 52 as the balloon operation section disposed in the remote controller 15, and one of the first balloon state display section 53 and the second balloon state display section 54 as the balloon state display section disposed in the remote controller 15 in accordance with the balloon to be used for the endoscope.

Although the electronic endoscope, in which the imaging elements are used to capture an image of a state of the subject and the captured image is observed, is used in the above embodiment, the present invention is not limited thereto. The present invention is applicable to an endoscope which adopts an optical image guide to observe a state of the subject.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A remote controller for a balloon controlling device, which is connected to a balloon controlling device for controlling swelling or contracting of a balloon to be used for an endoscope, the remote controller comprising:
   a first balloon operation button for performing an operation for swelling or contracting a first balloon, wherein the first balloon operation button includes a first state display section for displaying a swollen state and a contracted state of the first balloon, and
   a central axis passing through a central portion of the first state display section and a central axis passing through a central portion of the first balloon operation button are substantially coincident with each other.

2. The remote controller for a balloon controlling device according to claim 1, wherein
   the first balloon is attached to an insertion section of the endoscope.

3. The remote controller for a balloon controlling device according to claim 2 further comprising:
   a second balloon state display section for displaying a swollen state and a contracted state of a second balloon attached to an overtube covering over the insertion section of the endoscope; and
   a second balloon operation button for performing an operation for swelling or contracting the second balloon, the second balloon operation button including the second balloon state display section, wherein
   a central axis passing through a central portion of the second balloon state display section and a central axis passing through a central portion of the second balloon operation button are substantially coincident with each other.

4. The remote controller for a balloon controlling device according to claim 3, wherein the first balloon state display section and the second balloon state display section have a first and a second swollen-state display portions in the shape of a ring representing the swollen state respectively, and a first and a second contracted-state display portions having a flattened shape representing the contracted state respectively, the first and a second contracted-state display portion being disposed inside the first and a second swollen-state display portion respectively.

5. The remote controller for a balloon controlling device according to claim 4, wherein
   at least part of the first balloon operation button consists of a black member, and
   at least part of the second balloon operation button consists of a white member.

6. The remote controller for a balloon controlling device according to claim 4, further comprising an operation button disposed at a position different from a position at which the first and second balloon operation buttons are disposed, wherein
   the operation button has a shape different from a shape of the first and second balloon operation buttons.

7. The remote controller for a balloon controlling device according to claim 6, wherein each of the first and second balloon operation buttons has a circular outer shape.

8. The remote controller for a balloon controlling device according to claim 7, wherein the first and second swollen-state display portions are disposed along outer circumference of the first and second balloon operation buttons respectively.

9. The remote controller for a balloon controlling device according to claim 8, wherein the first and second contracted-state display portions are disposed inside the first and second balloon operation buttons respectively.

10. The remote controller for a balloon controlling device according to claim 4, wherein
    a light emitter is disposed inside each of the first and second swollen-state display portions and the first and second contracted-state display portions, and
    the first and second swollen-state display portions emit light in the swollen state, and the first and second contracted-state display portions emit light in the contracted state.

11. The remote controller for a balloon controlling device according to claim 1, wherein the first balloon operation button is a push button for switching the first balloon between the swollen state and the contracted state upon being pressed.

12. An endoscope system comprising:
    an endoscope having a first balloon attached to an insertion section of an endoscope;
    an overtube covered over the insertion section of the endoscope and having a second balloon;
    a balloon controlling device for controlling swelling or contracting of the first balloon and the second balloon; and
    a remote controller for a balloon controlling device including first and second balloon operation buttons for performing an operation for swelling or contracting the first balloon and the second balloon respectively,
    wherein the first balloon operation button includes a first state display section for displaying a swollen state and a contracted state of the first balloon,
    wherein the second balloon operation button includes a second state display section for displaying a swollen state and a contracted state of the second balloon,
    wherein a central axis passing through a central portion of the first state display section and a central axis passing through a central portion of the first balloon operation button are substantially coincident with each other, and
    wherein a central axis passing through a central portion of the second state display section and a central axis passing through a central portion of the second balloon operation button are substantially coincident with each other.

13. A remote controller for a balloon controlling device, which is connected to a balloon controlling device for controlling swelling or contracting of a balloon to be used for an endoscope, the remote controller comprising:
    a first balloon operation button for performing an operation for swelling or contracting a first balloon, wherein the first balloon operation button includes a first state display section for displaying a swollen state and a contracted state of the first balloon, and the first state display section is disposed on the first balloon operation button.

\* \* \* \* \*